United States Patent [19]

Curwen et al.

[11] Patent Number: 5,669,382
[45] Date of Patent: Sep. 23, 1997

[54] SYSTEM FOR MEASURING MYOCARDIUM IN CARDIAC IMAGES

[75] Inventors: Rupert William Meldrum Curwen, Ballston Lake; Richard Ian Hartley, Schenectady, both of N.Y.

[73] Assignee: General Electric Company, Schenectady, N.Y.

[21] Appl. No.: 751,345

[22] Filed: Nov. 19, 1996

[51] Int. Cl.$^6$ ................................................ A61B 6/00
[52] U.S. Cl. ................................ 128/653.1; 382/272
[58] Field of Search .................. 128/653.1, 653.2, 128/659, 660.07, 661.04, 661.01, 695, 713; 382/128, 130–132, 266, 270–273; 364/413.13, 413.25

[56] References Cited

U.S. PATENT DOCUMENTS

| | | | |
|---|---|---|---|
| 4,240,440 | 12/1980 | Groch et al. | 128/659 |
| 4,295,473 | 10/1981 | Diamond et al. | 128/695 |
| 4,936,311 | 6/1990 | Oe | 128/653.1 |
| 5,040,225 | 8/1991 | Gouge | 128/660.04 X |
| 5,107,838 | 4/1992 | Yamaguchi | 128/713 X |
| 5,148,809 | 9/1992 | Biegeleisen-Knight et al. | 128/660.07 |
| 5,239,591 | 8/1993 | Ranganath | 128/653.2 |
| 5,360,006 | 11/1994 | Geiser et al. | 128/653.1 |
| 5,435,310 | 7/1995 | Sheehan et al. | 128/653.1 |
| 5,469,850 | 11/1995 | Iizuka et al. | 128/660.07 |
| 5,568,811 | 10/1996 | Olstad | 128/660.07 |
| 5,570,430 | 10/1996 | Sheehan et al. | 128/653.1 |
| 5,601,084 | 2/1997 | Sheehan et al. | 128/653.1 |

OTHER PUBLICATIONS

"Constrained Deformable Superquadrics and Non-Rigid Motion Tracking" by D. Metaxas and D. Terzopoulos, IEEE Computer Vision and Pattern Recognition, pp. 337–343, 1991.

"Boundary Finding With Parametrically Deformable Models" by L.H. Staib and J.S. Duncan, IEEE Trans. Pattern Analysis and Machine Intelligence, 14 (11): Nov. 1992; pp. 1061–1075.

"Active Region Moidels for Segmenting Medical Images" by J. Irvins and J. Porrill, International Conference on Image Processing, 0-8186-6950-0/94 (1994), pp. 227–231.

*Primary Examiner*—Francis Jaworski
*Attorney, Agent, or Firm*—Lawrence P. Zale; Marvin Snyder

[57] ABSTRACT

The present invention determines the epicardial boundary, being a closed curve dividing the myocardium from the tissue and blood surrounding the left ventricle. A mean and standard deviation is determined for pixels of a medical image of the subject's myocardial tissue. These are used to define a "goodness function" over the image which is positive for pixels statistically likely to be myocardial tissue, and negative for other pixels. An initial curve for modeling the epicardium in radial coordinates starts with a curve of inner myocardial boundary obtained my conventional imaging techniques. This curve is then iteratively updated to maximize the total "goodness function" of the region encompassed.

3 Claims, 2 Drawing Sheets

SYSTEM FOR MEASURING MYOCARDIUM IN CARDIAC IMAGES

BACKGROUND OF THE INVENTION

1. Scope of the Invention

The present invention relates to medical cardiac measurement, and more specifically to measurement of cardiac muscle from a series of medical images.

2. Related Prior Art

It is sometimes necessary to be able to segment contiguous regions of the same material within a subject into different anatomical features from images acquired of the subject. In order to correctly diagnose heart disease, structures of the subject's heart must be identified from cardiac images. Conventional method are known for segmenting structures which may be used for identifying a subject's left ventricle, which also defines the interior boundary of the subject's myocardium. For measurements of such parameters such as myocardium thickness and motion, it is also necessary to identify the outer boundary of the myocardium, known as the epicardium.

Image intensity thresholding techniques will not work well for identification of the epicardium, since the myocardium lies adjacent to tissue of similar intensity. Previous techniques for detection of the epicardium have generally been based on deformable templates, or "snakes". A publication "Constrained Deformable Superquadrics And Non-Rigid Motion Tracking", by D. Metaxas and D. Terzopoulos, *IEEE Computer Vision and Pattern Recognition*, pp. 337–343, 1991 describes using 3-dimensional snakes to model the epicardium. The problem with such 3D techniques is that they are in general too slow for clinical applications.

Two-dimensional snake techniques have also been applied in the past. For instance, a type of 'Fourier snake' described in "Boundary Finding With Parametrically Deformable Models" by L. H. Staib and J. S. Duncan, pp. 1061–1075, *IEEE Trans. Pattern Analysis and Machine Intelligence*, 14(11): November 1992 has been applied to this problem. While 2D snake methods propose a sophisticated model for representing shape, they use only image gradient based measurements of the boundary. These require the initial estimate of model position to be close to the correct solution, and also are poor at detecting low contrast but statistically significant boundaries, as are often found in cardiac MR images.

Currently, there is a need for a quick and accurate system for determining myocardial boundaries for more accurate cardiac diagnosis.

SUMMARY OF THE INVENTION

A system for determining an epicardial boundary from which may be measured myocardium thickness of a subject's heart is described. Cardiac images having pixel intensities $I(r,\theta)$, expressed in polar coordinates $(r,\theta)$ where the center of the polar coordinate system is taken to be the centroid of the ventricular region, are obtained by a medical imaging device capable of imaging blood pools. The radius is computed at several sample angles $\theta_i$, where $0 \leq \theta_i \leq 2\pi$, to give a sequence of radial measurements $r(\theta_i)$.

A myocardium inner boundary, being the outer boundary of the ventricle blood pool is identified and used as an initial curve $r(\theta_i)$. This may be performed by conventional means.

The myocardium inner boundary $r(\theta_i)$ is expanded by a predetermined number of image pixels n to create a boundary $M_l$, where n is less than ½ of an approximate myocardium thickness determined by expected values from past measurements of similar images.

$M_l$ is then expanded by a predetermined number of image pixels m to create a boundary $M_h$, where m is also less than ½ of an approximate myocardium thickness determined by measuring the image.

A mean image pixel intensity $\mu$ and standard deviation $\sigma$ of pixel intensities $I(r,\theta)$ in a region M between $M_h$ and $M_l$ is then determined.

A goodness function $G(I(r,\theta))$ is determined from $\mu,\sigma$, indicating when an intensity $I(r,\theta)$ for at $(r,\theta)$ can be statistically determined as myocardium;

Second derivative and fourth derivatives of radial change due to change in angle, $$\frac{\partial^2 r}{\partial \theta^2}, \frac{\partial^4 r}{\partial \theta^4},$$

respectively are calculated and combined with $G(I(r,\theta))$ to determine a localized energy function $H(\theta)$.

$r(\theta_i)$ is expanded by $\delta r(\theta_i)$, being $-\epsilon H(\theta_i)$, to determine a new boundary; and The above steps, starting with determining a goodness function, are repeated for a plurality of iterations until $H(\theta_i)$ is less than a predetermined amount, to result in an epicardial boundary $r(\theta_i)$.

OBJECTS OF THE INVENTION

An object of the present invention is to provide a system to measure the epicardium of a subject's heart.

It is another object of the present invention to measure epicardium thickness and motion.

It is another object of the present invention to determine cardiac functioning from a series of cardiac images.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

The Radial-model Region-Based Snake

Figure 1:
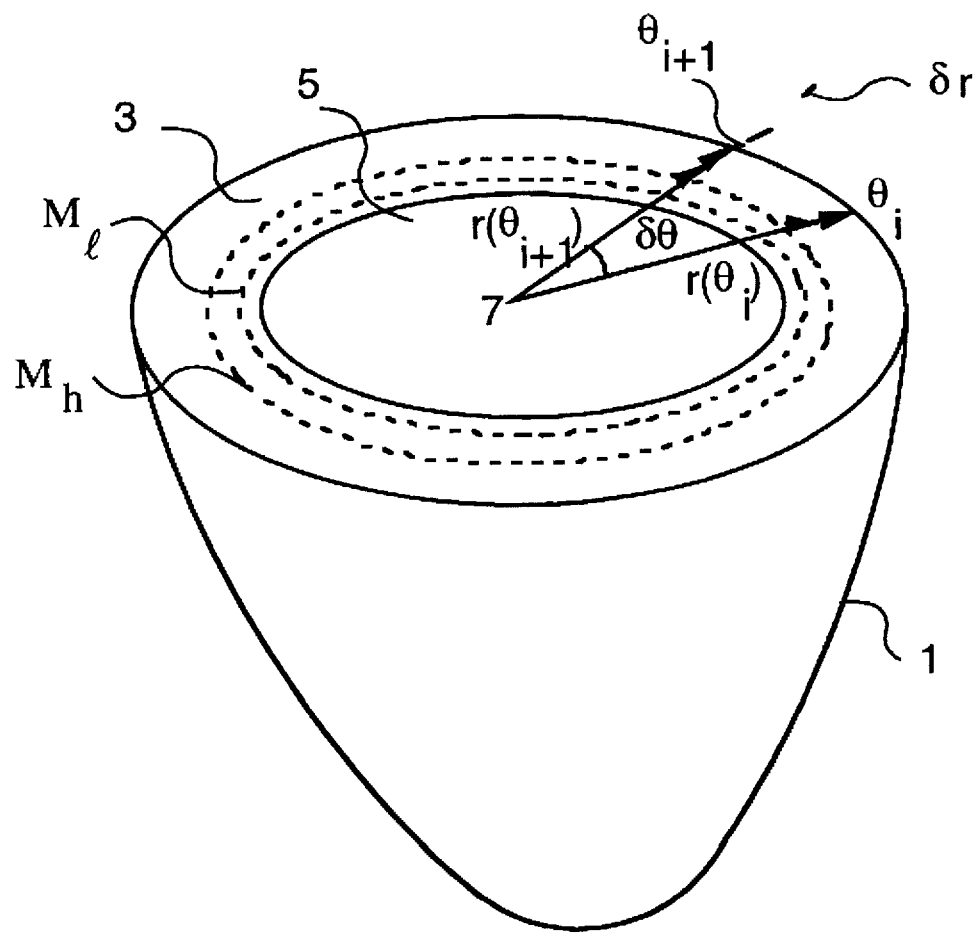
FIG. 1 is an illustration of a subject's heart showing the coordinate system used and portions of the heart to be measured.

In FIG. 1, a cross section of a subject's heart is shown. Here the outer surface 1 of the ventricle, an epicardial boundary, is sought to be used in further cardiac diagnostics.

In order to find epicardial boundary 1 robustly it is necessary to take advantage of the expected general shape of the region desired to be measured, such as the myocardium 3. Myocardium 3, as seen in a single slice image of FIG. 1 bisecting a long axis of a subject's ventricle, is an approximately annular-shaped region surrounding the left ventricle. Blood pool 5 is determined by conventional blood imaging and segmentation means.

The present invention employs a region-based snake assuming an annular model for the myocardium. A polar coordinate system based at a center 7 of a subject's ventricle is used to parameterize the snake. The region based snake model is similar to that described in "Active Region Models for Segmenting Medical Images" by J. Irvins and J. Porrill, pp. 227–231 IEEE International Conference on Image Processing, 0-8186-6950-0/94 (1994). This model is naturally suited to problems in which the region of interest is roughly circular and where the approximate centroid of the region has been determined in advance.

The present invention proceeds by working on a single image slice at a time. Let $I(r,\theta)$ be the intensity of a pixel at $(r,\theta)$ of the image, and $G(I(r,\theta))$ be a goodness function indicating type of tissue defined for all pixels in the image, to be described below. The epicardium is modeled by distance $r(\theta)$ from the origin. The snake method computes a parameterized curve that minimizes an "energy function" containing two terms representing curve constraints and a third term representing tissue type. The closer the modeled curve approximates an annular region the lower the energy contributed by the first two terms, and the closer the region is to the intensities of myocardium, the lower the energy contributed by the third term. The energy function of the present invention is as follows:

$$E = \frac{\alpha}{2} \oint_R \left( \frac{\partial r}{\partial \theta} \right)^2 d\theta + \frac{\beta}{2} \oint_R \left( \frac{\partial^2 r}{\partial \theta^2} \right)^2 d\theta + E_{region} \quad (1)$$

where $$E_{region} = -\gamma \iint_R G(I(r,\theta)) \, r \, dr \, d\theta \quad (2)$$

which $\iint_R$ is the integral of the goodness function $G(I(r,\theta))$ over the interior R of the model, and $\oint_R$ represents the integral around the curve. Two parameters $\alpha$, and $\beta$ defined the relative contributions of first and second order stiffness toward energy E, the first two terms in Eq. (1). The third parameter $\gamma$ determines the contribution of the goodness function towards energy E.

Note that the model in Eq. (1) is defined in the radial coordinates. Thus the lowest energy E is achieved when the curve is a circle, in the absence of external image forces.

The energy varies when the curve is altered by a small variation $\delta r(\theta)$. The calculus of variations may be used to derive an equation for the corresponding change in the energy of the curve. The result is that:

$$\delta E \approx \oint H(\theta) \delta r(\theta) d\theta \quad (3)$$

where $\delta(r)$ is a change in radial dimension, and $H(\theta)$ is defined as:

$$H(\theta) = \alpha \frac{\partial^2 r}{\partial \theta^2} - \beta \frac{\partial^4 r}{\partial \theta^4} + \gamma G(I(r,\theta)). \quad (4)$$

Discrete form

In practice, curves in the image are represented by sampling them for discrete values of $\theta$. Derivatives are then computed using finite differences. If the curve is sampled at discrete angles $\theta_0, \theta_1, \ldots$ separated by $\Delta\theta$, then symmetric differences in space are:

$$\frac{\partial^2 r}{\partial \theta^2} = \frac{1}{2(\Delta\theta)^2} \{r(\theta_{i+1}) - 2r(\theta_i) + r(\theta_{i-1})\} \quad (5)$$

-continued $$\frac{\partial^4 r}{\partial \theta^4} = \frac{1}{2(\Delta\theta)^4} \{r(\theta_{i+3}) - 2r(\theta_{i+2}) -$$

$$r(\theta_{i+1}) + 4r(\theta_i) - r(\theta_{i-1}) - 2r(\theta_{i-2}) + r(\theta_{i-3})\}$$

The integral of Eq. (3) now becomes:

$$\delta E \approx \sum_i H(\theta_i) \delta r(\theta_i) \quad (6)$$

Goodness function

The goodness function $G(I(r,\theta))$ is used to ensure that the snake converges to the epicardial boundary of the image. In the case of epicardial segmentation, the goodness function is defined as:

$$G(I(r,\theta)) = 1 - \frac{|I(r,\theta) - \mu|}{k\sigma} \quad (7)$$

where $I(r,\theta)$ is the image intensity of a pixel at $(r,\theta)$, $\mu$ and $\sigma$ are the mean and standard deviation of the intensity of the myocardial tissue in the image, and k is a constant, which may be predetermined. If the intensity of the pixel at $(r,\theta)$ is within k standard deviations of the mean, then the goodness function is positive statistically indicating myocardial tissue, otherwise it is negative statistically indicating tissues other than myocardium.

The parameters $\mu$ and $\sigma$ are determined using the a priori known ventricle region. This region is dilated by a fixed number of pixels n to form region $M_l$ provided n is chosen to be less than half the minimum width of the myocardium expected in the images, which can be determined from anatomical knowledge and the calibration of similar images. $M_l$ which in turn is dilated by a number of pixels, m which may or may not be equal to n, but must also be less than ½ of the myocardium minimum thickness to insure that this region, $M_h$, is still within the myocardium region. A new region is then formed $M = M_h - M_l$ which lies wholly within the myocardium. The parameters $\mu$ and $\sigma$ are then calculated as the mean and standard deviation of the intensities of pixels in M.

In general, the coordinates $(r,\theta)$ will not lie precisely on an image pixel. The value of $I(r,\theta)$ may be taken as the intensity of the nearest pixel, or else computed using linear or higher order interpolation.

Optimization

If one wishes to decrease the energy of the curve, it can be seen from Eq. (3) that this may be done by adjusting a step size:

$$\delta r(\theta) = -\epsilon H(\theta) \quad (8)$$

where $\epsilon$ is a small positive constant chosen so that $\delta r$ is a sufficiently small variation. With this choice of $\delta r(\theta)$ the integral in Eq. (3) is the integral of a negative function, and so $\delta E < 0$. Note also, that when $H(\theta) = 0$, the value of $\delta E$ is also zero for all small variations in the function. In other words, the curve is at a local energy minimum.

At each iteration, the value of $H(\theta)$ is computed at each angle $\theta_i$ using Eq. (4) and these finite difference formulae, Eq. (5).

The variation $\delta r(\theta)$ to be applied is then given by Eq. (8), where the constant $\epsilon$ is chosen so that the maximum value of $\delta r(\theta)$ is one pixel. This normalization ensures that the snake will not skip over detail in the image by expanding too rapidly.

This process of varying $\delta r(\theta)$ and calculating $r(\theta)$ is repeated until the steady state is reached, in which the snake oscillates gently around a fixed position, or until a maximum number of iterations is exceeded, in which case the segmentation has failed.

If H(θ) oscillates about zero then the small steps, δr, are also going to oscillate around zero, so the snake will oscillate gently around the correct solution.

Implementation

Figure 2:
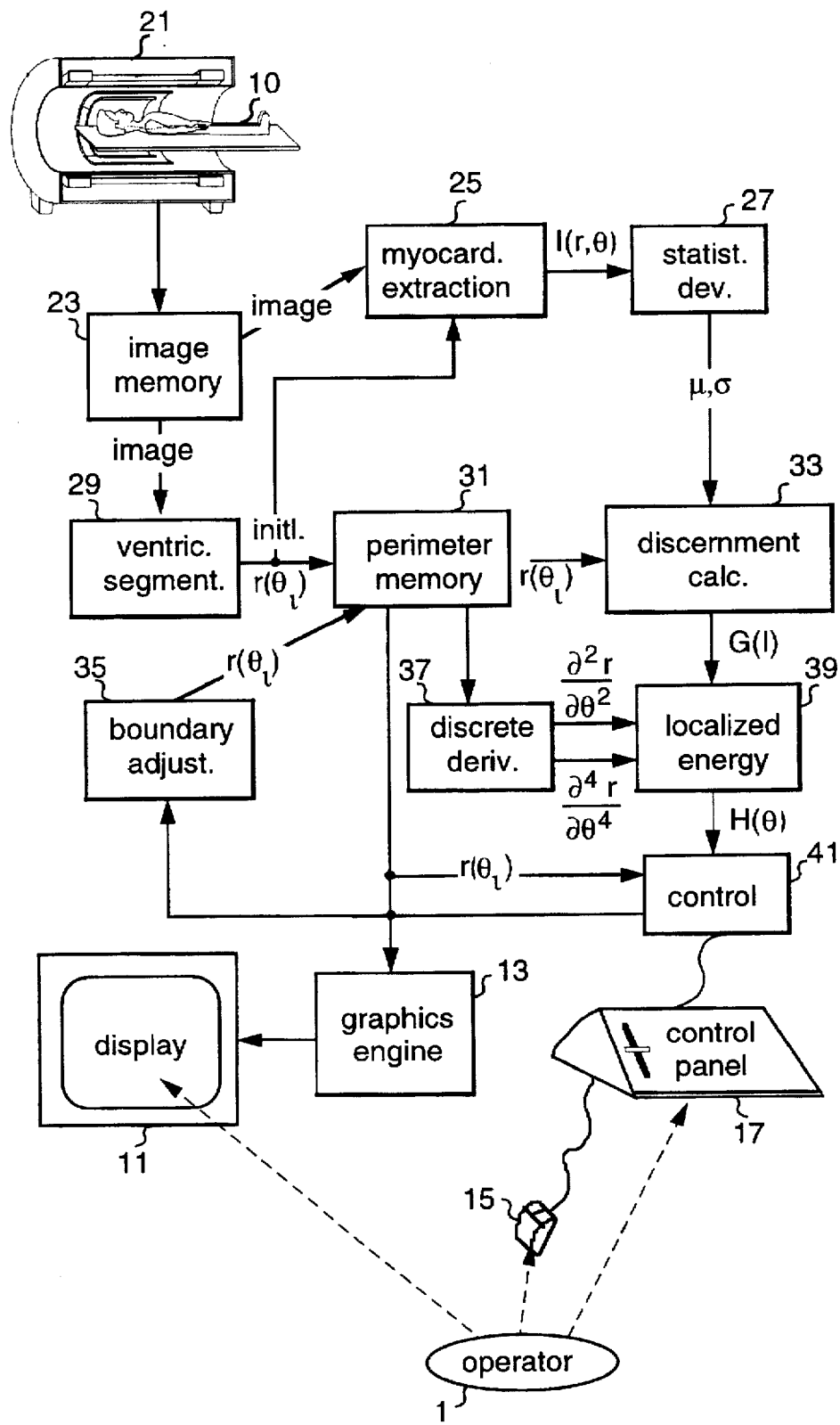
FIG. 2 is a simplified block diagram of an embodiment of the present invention.

In FIG. 2 a simplified block diagram of the present invention is shown. Each of these blocks represents a functional unit which maybe hardware, or hardware and software working in conjunction. Each block represents a specific function, which may or may not represent a single subroutine.

In block 21, a medical imaging device acquires a medical image being an array of intensities I(r,θ) of a subject 10. This medical imaging device must be capable of imaging blood pools and portions of the subject's heart. The images are passed to imaging memory 23 and stored there.

A myocardium extraction device 25 reads the image intensities I(r,θ). At least one image in image memory 23 is processed by a ventricle segmentation unit 29, which discerns the outline of the ventricular blood pool, which is an initial estimate of a perimeter $r(\theta_i)$. The initial ventricular perimeter, $r(\theta_i)$ is stored in a perimeter memory 31. The initial perimeter may be calculated by any conventional method available.

The ventricular outline is passed to myocardium extraction device 25 which expands the ventricular blood pool outline by an amount which is less than ½ of the approximate thickness of the myocardium wall. This approximate thickness may be determined by measuring the myocardium thickness of the image at its thinnest point, or else by knowledge of properties of prior images. This expanded region is called $M_l$. Region $M_l$ is then expanded again by an amount also less than ½ of the approximate myocardium wall thickness to define a second region $M_h$ encompassing region $M_l$. The region between $M_h$ and $M_l$, termed M, is passed to a statistical device 27 which determines the mean pixel intensity μ of this region and the standard deviation σ of this region.

Perimeter $r(\theta_i)$ is passed, either directly or through perimeter memory 31, to a discernment unit 33. Discernment unit 33 also receives the mean pixel intensity μ and standard deviation σ from statistical device 27. Discernment unit 33 then determines a "goodness function" G(I(r,θ)) for each of the pixels around the perimeter. Function G(I(r,θ)) is a measure of how closely the intensity I(r,θ) matches the mean intensity μ of the myocardium. Intensities which are more than k standard deviations away from the mean are determined to be some tissue other than myocardium and the G(I(r,θ)) function has a negative value for those.

The current perimeter $r(\theta_i)$ is also passed to a discrete derivative device 37 which determines the second derivative of radius with respect to θ and the fourth derivative of radius with respect to θ both of which are passed to a localized energy calculation device 39. Goodness function G(I(r,θ)) is also passed to device 39 which calculates a localized energy H(θ).

A control unit 41 receives the localized energy function H(θ) and determines if this localized energy function is above a predetermined threshold. If H(θ) is above the threshold, and a predetermines number of iterations have not yet been exceeded, and multiplies the energy function H(θ) by a multiplier −ε determined such that the product −εH(θ) is less than a single pixel width. −εH(θ) is used as δr, an incremental change to perimeter radius.

Incremental change δr is passed to a radius adjustment device 35 which takes the current perimeter $r(\theta_i)$ and adds to it δr to adjust the perimeter. The adjusted perimeter $r(\theta_i)$ is again stored in perimeter memory 31 and the process repeats until control unit 41 determines that the localized energy function is below a predetermined threshold, or a maximum number of iterations have been exceeded.

In the case where a maximum number of iterations have been exceeded and the energy function is not below a predetermined threshold, then the perimeter has failed to converge to an answer, and the operator is notified.

On the other hand, if the localized energy function is below the predetermined threshold, the resulting perimeter $r(\theta_i)$ converges to a epicardial boundary.

Since the inner boundary of the myocardium is known from conventional means, and the outer boundary of the myocardium, epicardium, is now known from the present invention, the thickness of the myocardium may be measured and used for various cardiac diagnostic tests.

Optionally, a graphics engine 13 may be used to display pertinent data on a display 11 such as the current perimeter $r(\theta_i)$ to an operator 1. Operator 1 may also interact with a control panel 17 or pointing device 15 to adjust predetermined parameters of the system, such as the minimum value of H(θ).

The present invention is capable of working on a single image, however, it may be used for multiple images of a cardiac cycles and therefore the cardiac wall thickness may be determined over the entire cardiac cycle. This provides valuable information as to the functioning of the subject's heart, and may be used in predicting health of the subject's heart, and for diagnosing possible heart disease.

Below is an outline of the functioning of the present invention.

1. The myocardium inner boundary is found using any conventional technique and the centroid of the left ventricle is chosen as the origin of a polar coordinate system
2. The mean and standard deviation (μ and σ) of pixels in the myocardial region are computed as the mean and standard deviation of intensities in a region $M=M_h-M_l$ surrounding the left ventricle.
3. Goodness function G(I(r,θ)) is determined using μ, θ and I(r,θ).
4. A curve surrounding the left ventricle, the inner boundary of the myocardium, is found using conventional imaging methods. This curve serves as an initial curve for the iterative snake algorithm. The curve is sampled at regular angles $\theta_i$ separated by Δθ to give a discrete representation of the curve.
5. The value of H(θ) is computed using equation Eqs. (4) and (5) and G(I(r,θ)), from Eq. (7).
6. The increment δr(θ) to be applied is computed using Eq. (8), where ε is a positive constant chosen so that the maximum value of $\delta r(\theta_i)$ is one pixel.
7. The curve $r(\theta_i)$ is expanded by adding $\delta r(\theta_i)$ to $r(\theta_i)$ for each i.
8. Steps 5–7 are repeated until the resulting curve $r(\theta_i)$ oscillates about a fixed curve,(H(θ) is below a predetermined threshold) or for a fixed maximum number of iterations. In the latter case, the method is deemed to have failed.
9. The resulting values $r(\theta_i)$ are used as the epicardial boundary.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A method of determining epicardial boundary of myocardium of a subject's from a cardiac image having pixel intensities at $(r,\theta)$ of $I(r,\theta)$ comprising the steps of:
   a) identifying a myocardium inner boundary of said image $r(\theta)$ at several discrete angles $\theta_i$ from said image by conventional means;
   b) determining a goodness function $G(I(r,\theta))$ being positive if pixel intensity $I(r,\theta)$ at $(r,\theta)$ is deemed to be myocardium, and negative is other tissue, for a plurality of $(r,\theta)$ coordinates;
   c) calculating the second derivative and fourth derivatives of radial change due to change in angle, $$\frac{\partial^2 r}{\partial \theta^2}, \frac{\partial^4 r}{\partial \theta^4},$$

respectively;
   d) calculating a localized energy function $H(\theta)$ from $G(I(r,\theta))$, $$\frac{\partial^2 r}{\partial \theta^2}, \frac{\partial^4 r}{\partial \theta^4},$$

$\alpha, \beta, \gamma$ employing calculus of variation;
   e) determining $\delta r(\theta_i)$ from $-\epsilon H(\theta)$ where $\epsilon$ is selected to make the product $|-\epsilon H(\theta)|$ less than a single pixel width;
   f) adding $dr(\theta_i)$ to each value of $r(\theta_i)$ to determine a new boundary; and
   g) repeating steps "c"–"f" for a plurality of iterations to result in an epicardial boundary $r(\theta_i)$.

2. The method of determining epicardial boundary of claim 1 wherein the step of determining a goodness function $G(I(r,\theta))$ comprises the steps of:
   a) expanding the myocardium inner boundary $r(\theta_i)$ by a predetermined number of image pixels n to create a boundary $M_l$, where n is less than ½ of an approximate myocardium thickness determined by measuring the image;
   b) expanding $M_l$ by a predetermined number of image pixels m to create a boundary $M_h$, where m is less than ½ of an approximate myocardium thickness determined by measuring the image;
   c) determining a mean image pixel intensity $\mu$ and standard deviation $\sigma$ of pixel intensities $I(r,\theta)$ in a region M between $M_h$ and $M_l$; and
   d) calculating $G(I(r,\theta))$ according to:

$$G(I(r,\theta)) = 1 - \frac{|I(r,\theta) - \mu|}{k\sigma}.$$

3. The method of determining epicardial boundary of claim 1 wherein the step of calculating localized energy function $H(\theta)$ comprises the steps of evaluating:

$$H(\theta) = \alpha \frac{\partial^2 r}{\partial \theta^2} - \beta \frac{\partial^4 r}{\partial \theta^4} + \gamma G(I(r,\theta)).$$

* * * * *